United States Patent [19]
Halazy et al.

[11] Patent Number: 6,110,917
[45] Date of Patent: Aug. 29, 2000

[54] METHANESULPHONATE SALT OF AN ARYLPIPERAZINE DERIVED FROM TRYPTAMINE AND ITS SOLVATES FOR PHARMACEUTICAL USE

[75] Inventors: Serge Halazy, Lagarrigue; Michel Perez, Castres, both of France

[73] Assignee: Pierre Fabre Medicament, France

[21] Appl. No.: 09/202,539

[22] PCT Filed: Jun. 12, 1997

[86] PCT No.: PCT/FR97/01053

§ 371 Date: Dec. 16, 1998

§ 102(e) Date: Dec. 16, 1998

[87] PCT Pub. No.: WO97/48680

PCT Pub. Date: Dec. 24, 1997

[30] Foreign Application Priority Data

Jun. 17, 1996 [FR] France .................................. 96 07491

[51] Int. Cl.[7] .......................... A01N 43/60; A61K 31/495
[52] U.S. Cl. ........................................ 514/254.09; 514/336
[58] Field of Search ........................ 514/254.09; 544/336

[56] References Cited

FOREIGN PATENT DOCUMENTS

| 0 490 689 A1 | 6/1992 | European Pat. Off. . |
| 2 162 522 | 2/1986 | United Kingdom . |
| 2 185 020 | 7/1987 | United Kingdom . |
| WO 95/14004 | 5/1995 | WIPO . |

*Primary Examiner*—Dwayne C. Jones
*Attorney, Agent, or Firm*—Finnegan, Henderson, Farabow, Garrett & Dunner, L.L.P.

[57] ABSTRACT

The invention discloses the methanesulphonate salt of 4-(4-{2-[3-(2-amino-ethyl)-1H-indol-5-yloxy]-acetyl}-piperazin-1-yl)-benzonitrile, its solvates or hydrates as well as the preparation of the said salt. The invention also discloses the pharmaceutical compositions containing the said salt, useful in the preparation of medicines for treating vasospastic disorders.

18 Claims, No Drawings

METHANESULPHONATE SALT OF AN ARYLPIPERAZINE DERIVED FROM TRYPTAMINE AND ITS SOLVATES FOR PHARMACEUTICAL USE

This application is a 371 of PCT/FR97/01053, filed on Jun. 12, 1997.

The subject-matter of the present invention is a specific salt of an active pharmaceutical agent. More particularly, the invention relates to the methanesulfonate salt of an arylpiperazide derived from tryptamine which acts at the level of the serotonin (5-HT) receptors, more specifically as selective agonist of $5\text{-HT}_{1D/1B}$ receptors. This compound is consequently found to be of use in the treatment of pathological conditions for which a selective agonist of these receptors is indicated.

Agonists of the $5\text{-HT}_{1D/1B}$ receptors (according to the recent nomenclature proposed in TiPS, 17, 103, 1996) which demonstrate a selective vasoconstrictive activity have recently been described as useful in the treatment of migraine (cf., for example, A. Doenicke et al., The Lancet, 1, 1309, 1988). The salt of the present invention, which shows a powerful agonist activity at the level of the $5\text{-HT}_{1D/1B}$ receptors, is consequently particularly useful in the treatment, both curative and preventive, of classic migraine (with aura), common migraine (without aura) and associated or closely related disorders, such as vasospastic disorders, vascular facial pain or chronic vascular headaches.

Patent Application PCT FR 9401343 (WO-9514004) discloses a class of arylpiperazines derived from indole as selective and effective agonists of $5\text{-HT}_{1D/1B}$ receptors and consequently as particularly useful in the treatment of migraine and associated disorders.

The present invention relates to the mesylate (or methanesulfonate) salt of 4-(4-{2-[3-(2-aminoethyl)-1H-indol-5-yloxy]acetyl}piperazin-1-yl)benzonitrile of formula (I):

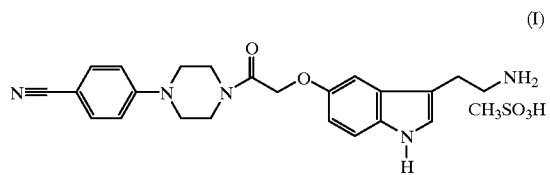

(I)

and its solvates (in particular its hydrates) which are acceptable for the therapeutic use.

The pharmaceutically acceptable salts of 4-(4-{2-[3-(2-aminoethyl)-1H-indol-5-yloxy]acetyl}piperazin-1-yl)benzonitrile form part, in a general way, of Patent Application WO-9514004. In fact, the hydrochloride, hydrobromide, sulfate, maleate and fumarate salts are specifically referred to in Application WO-9514004. However, this patent application in no case describes or suggests the specific salt of formula (I) forming part of the present invention.

The salt of formula (I) above, in an entirely unexpected way, possesses attractive advantages, in particular for its use as therapeutic agent. For example, the compound of formula (I) exhibits a solubility which is markedly greater than the other salts of 4-(4-{2-[3-(2-aminoethyl)-1H-indol-5-yloxy] acetyl}piperazin-1-yl)benzonitrile specifically claimed in Application WO-9514004.

Another aspect of the present invention has as subject-matter the compositions for pharmaceutical use comprising the methanesulfonate salt (I) in combination with one or more pharmaceutical vehicles which are acceptable for the therapeutic use.

The present invention also relates to the medicaments comprising at least one compound of formula (I) in the pure state or in the form of a composition in which it is combined with any other pharmaceutically compatible product, which can be inert or physiologically active. The medicaments according to the invention can be employed orally, parenterally, rectally or nasally or by any other administration route.

Tablets, pills, powders (gelatin capsules or cachets) or granules can be used as solid compositions for oral administration. In these compositions, the active principle according to the invention is mixed with one or more inert diluents, such as starch, cellulose, sucrose, lactose or silica, under an argon stream. These compositions can also comprise substances other than diluents, for example one or more lubricating agents, such as magnesium stearate or talc, a colorant, a coating agent (dragees) or a varnish.

Pharmaceutically acceptable solutions, suspensions, emulsions, syrups and elixirs comprising inert diluents, such as water, ethanol, glycerol, vegetable oils or liquid paraffin, can be used as liquid compositions for oral administration. These compositions can comprise substances other than the diluents, for example wetting, sweetening, thickening, flavoring or stabilizing products.

The sterile compositions for parenteral administration can preferably be suspensions, emulsions or non-aqueous or aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other sterile injectable medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eyedrops, mouthwashes, nose-drops or aerosols.

The doses depend on the desired effect, on the duration of the treatment and on the administration route used; they are generally between 0.0001 g and 1 g (preferably between 0.0005 g and 0.25 g) per day, preferably orally or nasally, for an adult with unit doses ranging from 0.05 mg to 500 mg of active substance and preferably from 0.5 mg to 50 mg.

Generally, the doctor will determine the appropriate dosage depending on the age, weight and all the other factors specific to the subject to be treated. The following examples illustrate compositions according to the invention [in these examples, the term "active component" denotes the compound of formula (I) defined as above:

TABLETS

They can be prepared by direct compression or by passing through a wet granulation. The procedure by direct compression is preferred but it may not be suitable in all cases, depending on the doses of the active component.

| A - By direct compression | |
|---|---|
| | mg for one tablet |
| Active component | 10.0 |
| Microcrystalline cellulose, B.P.C. | 89.5 |
| Magnesium stearate | 0.5 |
| | 100.0 |

The active component is passed through a sieve with a mesh size of 250 μm per side, mixing is carried out with the excipients and compression is carried out using 6.0 mm dies. Tablets having other mechanical strengths can be prepared by modifying the compressive weight with use of appropriate dies.

| B - Wet granulation | |
|---|---|
| | mg for one tablet |
| Active component | 10.0 |
| Lactose, pharmaceutical grade | 74.5 |
| Starch, pharmaceutical grade | 10.0 |
| Pregelatinized maize starch, pharmaceutical grade | 5.0 |
| Magnesium stearate | 0.5 |
| Weight at compression | 100.0 |

The active component is passed through a sieve with a mesh size of 250 μm and mixing is carried out with the lactose, the starch and the pregelatinized starch. The mixed powders are moistened with purified water, granulation is carried out, drying is carried out, sieving is carried out and mixing with the magnesium stearate is carried out. The lubricated granules are compressed as in the direct compression formulae. A thin coating layer can be applied to the tablets by means of appropriate film-forming materials, for example methylcellulose or hydroxypropylmethylcellulose, according to conventional techniques. The tablets can also be coated with sugar.

| Capsules | |
|---|---|
| | mg for one capsule |
| Active component | 10.0 |
| *Starch 1500 | 89.5 |
| Magnesium stearate, pharmaceutical grade | 0.5 |
| Filling weight | 100.0 |

*a form of directly compressible starch supplied by the firm Colorcon Ltd, Orpington, Kent, United Kingdom.

The active component is passed through a sieve with a mesh size of 250 μm and mixing with the other substances is carried out. The mixture is introduced into hard gelatin No. 2 capsules on a suitable filling machine. Other dosage units can be prepared by modifying the filling weight and, when necessary, by changing the size of the capsule.

| Syrup | |
|---|---|
| | mg per dose of 5 ml |
| Active component | 10.0 |
| Sucrose, pharmaceutical grade | 2750.0 |
| Glycerol, pharmaceutical grade | 500.0 |
| Buffer ) | q.s. |
| Flavoring ) | |
| Colorant ) | |
| Preservative ) | |
| Distilled water | 5.0 |

The active component, the buffer, the flavoring, the colorant and the preservative are dissolved in part of the water and the glycerol is added. The remainder of the water is heated to 80° C. and the sucrose is dissolved therein and the solution is then cooled. The two solutions are combined, the volume is adjusted and mixing is carried out. The syrup obtained is clarified by filtration.

| Suppositories | |
|---|---|
| Active component | 10.0 mg |
| *Witepsol H15 | remainder to 1.0 g |

*Tradename for Adeps Solidus from the European Pharmacopeia.

A suspension of the active component in Witepsol H15 is prepared and it is introduced into an appropriate machine with 1 g suppository molds.

| Liquid for administration by intravenous injection | |
|---|---|
| | g/l |
| Active component | 2.0 |
| Water for Injection, pharmaceutical grade | remainder to 1000.0 |

It is possible to add sodium chloride in order to adjust the tonicity of the solution and to adjust the pH to the maximum stability and/or in order to facilitate dissolution of the active component by means of a dilute alkali or acid or by adding appropriate buffer salts. The solution is prepared, is clarified and is introduced into phials of appropriate size which are sealed by melting the glass. It is also possible to sterilize the liquid for injection by heating in an autoclave according to one of the acceptable cycles. It is also possible to sterilize the solution by filtration and to introduce into a sterile phial under aseptic conditions. The solution can be introduced into the phials under a gaseous atmosphere.

| Cartridges for inhalation | |
|---|---|
| | g/cartridge |
| Micronized active component | 1.0 |
| Lactose, pharmaceutical grade | 39.0 |

The active component is micronized in a fluid-energy mill and converted to the form of fine particles before mixing with lactose for tablets in a high energy mixer. The pulverulent mixture is introduced into hard gelatin No. 3 capsules on an appropriate encapsulating machine. The contents of the cartridges are administered using a powder inhaler.

The oral administration of an antimigraine can encounter certain problems, insofar as the migraine (and other closely related or associated pathological conditions) is sometimes accompanied by nausea and vomiting, which make it difficult to tolerate oral administration of medicaments. Consequently, the administration of an antimigraine by the nasal route constitutes a particularly advantageous alternative.

The salt of formula (I) turns out to be, surprisingly, much more soluble in water (cf. Table 1) than the other salts derived from the same amino base and disclosed in Patent Application WO-9514004.

TABLE 1

Comparison of the solubility in water of various salts of 4-(4-{2-[3-(2-aminoethyl)-1H-indol-5-yloxy]acetyl}piperazin-1-yl)benzonitrile

| SALT | SOLUBILITY* |
|---|---|
| Methanesulfonate (compound I) | 4.0 |
| Hydrochloride | 0.87 |
| Sulfate | <1 |
| Maleate | <1 |
| Fumarate | <1 |

*expressed as mg of base per ml of water

The compound (I) of the present invention can consequently be particularly valued for its therapeutic use in the dissolved form and in particular for its use via nasal or oral administration. The present invention thus comprises a pharmaceutical composition suited to nasal or oral administration, which composition comprises the methanesulfonate salt of formula (I) in combination with one or more vehicles which are acceptable for the therapeutic use.

The solutions used for the administration of the compound of formula (I) are generally aqueous solutions prepared from water itself (for example, sterile water) or from water and a pharmaceutically acceptable cosolvent, such as, for example, ethanol, propylene glycol or polyethylene glycols. Such solutions can optionally comprise other excipients, such as preserving agents (for example, benzalkonium chloride or phenethyl alcohol), buffer agents, agents favorable for adjusting the osmotic pressure (for example, NaCl), flavoring agents (such as, for example, menthol, eucalyptol or camphor) or sweetening agents (for example, saccharin or aspartam).

The solutions for nasal administration are applied directly in the intranasal cavity by conventional means, using, for example, a dropper, a pipette or a spray. The formulation can be envisaged for administration as a single dose or in the form of repeated doses. Intranasal administration can also be carried out by means of a formulation of aerosol type, in which the compound of formula (I) is available in a bottle pressurized with a propellant gas, such as a chlorofluorocarbon (CFC) or carbon dioxide.

A pharmaceutical composition appropriate for nasal administration which is particularly valued and which forms part of the present invention comprises the salt of formula (I) in the form of an aqueous solution.

The aqueous solutions of the salt (I) which is claimed in the present invention for intranasal administration will preferably have a pH of between 4 and 8 and more particularly between 5 and 7. The aqueous solutions of the methanesulfonate salt of formula (I) are prepared by dissolving the salt of formula (I) in water. An alternative method for the preparation of aqueous solutions of the methanesulfonate salt of formula (I) consists in mixing a molar equivalent of 4-(4-{2-[3-(2-aminoethyl)-1H-indol-5-yloxy]acetyl}piperazin-1-yl)benzonitrile with 1.0 to 1.2 molar equivalents of methanesulfonic acid, preferably 1.0 equivalent, in water.

For intranasal administration, the aqueous solutions of the salt of formula (I) according to the present invention will preferably comprise the salt at a concentration of between 1 mg/ml and 4 mg/ml and preferably from 1.5 mg/ml to 4 mg/ml.

The present invention also comprises a process for manufacture of the mesylate salt of formula (I) as defined above, which consists in treating an intermediate of formula (II)

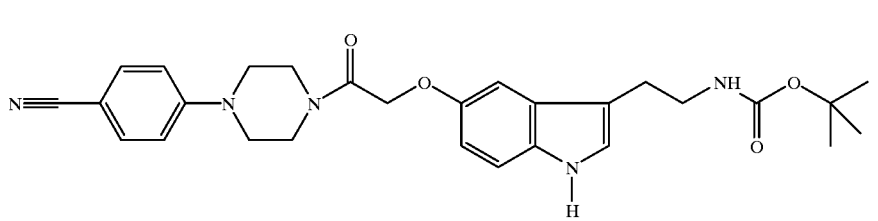

(II)

with methanesulfonic acid at a temperature of between 0° C. and 80° C., either in water or in an organic solvent, such as chloroform, dichloromethane, dichloroethane, THF, ethyl ether, dioxane, DMF or nitromethane, or alternatively in a water/THF, water/dioxane, water/acetone or water/DMF mixture. A particularly valued method for preparing the methanesulfonate salt of formula (I) consists in treating the N-t-butoxy-carbonyl derivative of formula (II) with 1 to 3 equivalents of methanesulfonic acid in chloroform at a temperature of between 15 and 30° C.

The compound of formula (II) described above is prepared by various methods and techniques well known to a person skilled in the art for preparing derivatives of this type, such as, for example, those disclosed in Patent Application WO-9514004. A particularly valued method for the preparation of the compound of formula (II) consists in condensing the arylpiperazine of formula (III)

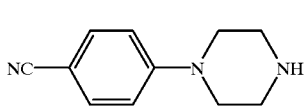

(III)

with the carboxylic acid of formula (IV) or one of its derivatives appropriate for condensation with an amine with the aim of preparing an amide

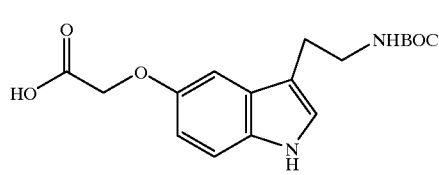

(IV)

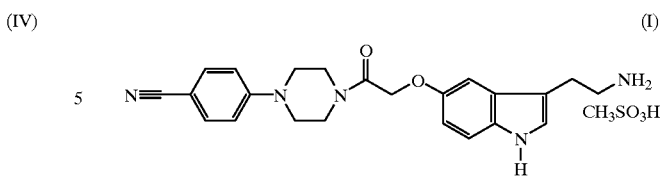

(I)

The condensation of the carboxylic acid of formula (IV) with the arylpiperazine of formula (III) will be carried out by methods and techniques well known to a person skilled in the art for the preparation of amides from amines and carboxylic acids, which methods comprise the use of derivatives of the carboxylic acid of formula (IV), such as the corresponding acid chloride. A particularly valued method for the preparation of the intermediate of formula (II) consists in activating the intermediate (IV) by treatment with ethyl chloroformate in an organic solvent, such as dichloromethane, at a temperature of between −5° C. and −20° C. in the presence of a base, such as N-methylmorpholine. The reaction with the piperazine (III) at a temperature ranging from −15° C. to 25° C. results in the intermediate (II) with a yield of 82%.

The following procedure illustrates the method for the preparation of the salt of formula (I) from the intermediate (II):

The intermediate (II) (1.3 g, 2.58 mmol), in solution in dichloromethane (50 ml), is treated at room temperature with methanesulfonic acid (0.335 ml, 5.16 mmol). The mixture is stirred for 24 hours and then the white precipitate formed is filtered off on sintered glass and washed with a 2/1 dichloro-methane/ethanol mixture (20 ml) and with ether (30 ml). The crystals thus obtained are dried under vacuum to result in the compound (I) (1.12 g, 87%).

Elemental analysis ($C_{24}H_{29}N_5O_5S.0.60H_2O$)

% Calculated: C: 56.08, H: 6.00, N: 13.63 % Found: C: 55.91, H: 5.80, N: 13.63

$^1$H NMR, $d_6$-DMSO (ppm): 2.33 s, 3H; 2.90–3.10 m, 4H; 3.45 m, 4H; 3.63 m, 4H; 4.80 s, 2H; 6.79 dd, 1H; 7.02 d, 2H; 7.09 d, 1H; 7.19 d, 1H; 7.25 d, 1H; 7.60 d, 2H; 7.75 broad s, 3H; 10.83 s, 1H Melting point: 142° C.

What is claimed is:

1. A methanesulfonate salt of 4-(4-{2-[3-(2-aminoethyl)-1H-indol-5-yloxy]acetyl}piperazin-1-yl)benzonitrile of the formula:

and its pharmaceutically acceptable hydrates or solvates.

2. A pharmaceutical composition comprising a compound of the formula (I) as claimed in claim 1 in combination with a pharmaceutically acceptable vehicle.

3. A pharmaceutical composition as claimed in claim 2, in the form of an aqueous solution.

4. A pharmaceutical composition as claimed in claim 3, further comprising the salt of formula (I) at a concentration of between 1 and 4 mg/ml in the aqueous solution.

5. A pharmaceutical composition as claimed in claim 2, in the form of a tablet, pill, powder, capsule, cachet, or granule.

6. A pharmaceutical composition as claimed in claim 2, in the form of a solution, suspension, emulsion, syrup, or elixer.

7. A pharmaceutical composition as claimed in claim 6, wherein the solution is a non-aqueous solution.

8. A suppository or rectal capsule comprising the pharmaceutical composition as claimed in claim 2.

9. A pharmaceutical composition as claimed in claim 2, in the form of a cream, lotion, eyedrops, mouthwash, nosedrops, or aerosol.

10. A process for the preparation of the salt of formula (I) as claimed in claim 1, which comprises treating a derivative of the formula:

(II)

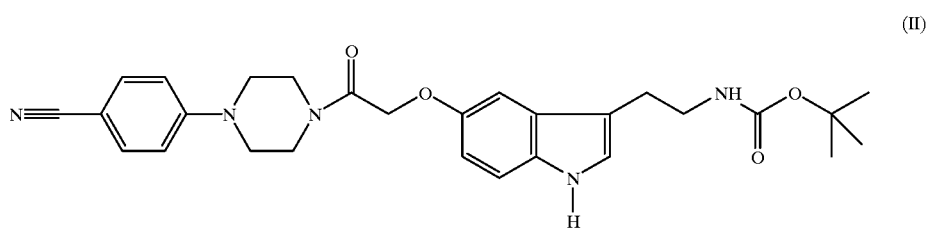

with methanesulfonic acid in a solvent.

11. A process as claimed in claim 10, wherein the derivative of formula (II) is treated with methanesulfonic acid at a temperature between 0° C. and 80° C.

12. A process as claimed in claim 10, wherein the solvent is water, chloroform, dichloromethane, dichloroethane, tetrahydrofuran ("THF"), ethyl ether, dioxane, N,N-dimethylformamide ("DMF"), or nitromethane.

13. A process as claimed in claim 10, wherein the solvent is a mixture of water and THF, dioxane, acetone, or DMF.

14. A process as claimed in claim 10, wherein a N-t-butoxy-carbonyl derivative of formula (II) is treated with 1 to 3 equivalents of methanesulfonic acid in chloroform at a temperature between 15° C. and 30° C.

15. A method of treating a subject afflicted with pain, which comprises administering to the subject a pain reducing amount of the methanesulfonate salt as claimed in claim 1.

16. A method of treating a subject afflicted with pain, which comprises administering the methanesulfonate salt as claimed in claim 1 in an amount sufficient to treat a subject, preventatively or curatively, for migraines, facial vascular pain, or chronic headaches.

17. A method as claimed in claim 15 or 16, which comprises administering to the subject 0.0001 g to 1 g per day of the methanesulfonate salt.

18. A method as claimed in claim 15 or 16, which comprises administering one or more unit doses ranging from 0.05 mg to 500 mg of the methanesulfonate salt.

* * * * *